(12) United States Patent
Hardy et al.

(10) Patent No.: US 10,320,752 B2
(45) Date of Patent: Jun. 11, 2019

(54) GRADIENTS OVER DISTRIBUTED DATASETS

(71) Applicant: National ICT Australia Limited, Eveleigh, New South Wales (AU)

(72) Inventors: Stephen Hardy, Eveleigh (AU); Felix Lawrence, Eveleigh (AU); Daniel Visentin, Eveleigh (AU)

(73) Assignee: National ICT Australia Limited, Eveleigh, New South Wales (AU)

( * ) Notice: Subject to any disclaimer, the term of this patent is extended or adjusted under 35 U.S.C. 154(b) by 0 days.

(21) Appl. No.: 15/521,409

(22) PCT Filed: Oct. 26, 2015

(86) PCT No.: PCT/AU2015/050661
§ 371 (c)(1),
(2) Date: Apr. 24, 2017

(87) PCT Pub. No.: WO2016/061635
PCT Pub. Date: Apr. 28, 2016

(65) Prior Publication Data
US 2017/0310643 A1 Oct. 26, 2017

(30) Foreign Application Priority Data
Oct. 24, 2014 (AU) ................................ 2014904260

(51) Int. Cl.
*G06F 21/00* (2013.01)
*H04L 29/06* (2006.01)
(Continued)

(52) U.S. Cl.
CPC ...... *H04L 63/0414* (2013.01); *G06F 21/6254* (2013.01); *G06Q 50/01* (2013.01);
(Continued)

(58) Field of Classification Search
CPC ........... G06F 17/30539; G06F 21/6245; G06F 17/30569; G06F 21/6254; G06F 21/6218;
(Continued)

(56) References Cited

U.S. PATENT DOCUMENTS 5,341,427 A * 8/1994 Hardy ................... H04L 9/0844
380/273
8,375,030 B2 2/2013 Rane et al.
(Continued)

FOREIGN PATENT DOCUMENTS

WO 2013/067542 A1 5/2013

OTHER PUBLICATIONS

Rajkumar, A. et al. A Differentially Private Stochastic Gradient Descent Algorithm for Multiparty Classification, Proceedings of the 15th International Conference on Artificial Intelligence and Statistics (AISTATS) 2012, La Palma, Canary Islands. Volume XX of JMLR: W&CP XX pp. 933-941, [online][retrieved from the Internet Jan. 4, 2016] <URL: http://jmir.csail.mit.edu/proceedings/papers/v22/rajkumar12/rajkumar12.pdf>.
(Continued)

*Primary Examiner* — Edward Zee
*Assistant Examiner* — Ka Shan Choy
(74) *Attorney, Agent, or Firm* — Kilpatrick Townsend & Stockton LLP (57) ABSTRACT

This disclosure relates to characterising data sets that are distributed as multiple data subsets over multiple computers such as by determining a gradient of an objective function. A computer determines a partial gradient of the objective function over a data subset stored on the computer and determines random data. The computer then determines an altered gradient by modifying the partial gradient based on the random data and encrypts the altered gradient such that one or more operations on the altered gradient can be
(Continued)

performed based on the encrypted gradient and sends the encrypted gradient. Since the partial gradient is altered based on random data and encrypted it is difficult for another computer to calculate the data that is stored on the first computer. This is an advantage as it allows to preserve the privacy of the data stored on the first computer while still allowing to characterise the data set.

17 Claims, 8 Drawing Sheets

(51) Int. Cl.
*G06F 21/62* (2013.01)
*G06Q 50/00* (2012.01)
*H04L 9/06* (2006.01)
*H04L 9/00* (2006.01)
*G06F 19/24* (2011.01)
*G06F 19/28* (2011.01)

(52) U.S. Cl.
CPC ............... *H04L 9/008* (2013.01); *H04L 9/06* (2013.01); *G06F 19/24* (2013.01); *G06F 19/28* (2013.01)

(58) Field of Classification Search
CPC ....... G06F 21/62; G06F 21/60; H04L 65/403; H04L 63/0428; H04L 63/0407; H04L 63/0414; H04L 9/06; H04L 63/04; H04L 29/06; H04L 9/008; G06N 99/005; G06Q 50/01; G06Q 50/00; G06Q 10/00
See application file for complete search history.

(56) References Cited

U.S. PATENT DOCUMENTS

| | | | | |
|---|---|---|---|---|
| 9,166,789 | B2* | 10/2015 | Ikeda | .................. H04L 9/003 |
| 2007/0118492 | A1* | 5/2007 | Bahlmann | ............ G06K 9/6278 |
| | | | | 706/20 |
| 2009/0150362 | A1* | 6/2009 | Evenhaim | ............ G06F 21/6254 |
| 2010/0030764 | A1* | 2/2010 | Koren | ............... G06F 17/30029 |
| | | | | 705/7.29 |
| 2011/0029809 | A1* | 2/2011 | Dhuse | .................. G06F 11/1076 |
| | | | | 714/6.1 |
| 2012/0237082 | A1* | 9/2012 | Sengupta | ........... G06K 9/00771 |
| | | | | 382/103 |
| 2013/0282679 | A1 | 10/2013 | Khin et al. | |
| 2014/0234845 | A1* | 8/2014 | Poritz | ................. B01L 3/50273 |
| | | | | 435/6.12 |
| 2015/0262095 | A1* | 9/2015 | Rajasekaran | ...... G06Q 10/0635 |
| | | | | 705/7.28 |
| 2015/0288662 | A1 | 10/2015 | Bilogrevic et al. | |
| 2016/0099807 | A1* | 4/2016 | Isshiki | .................... G06F 21/31 |
| | | | | 713/168 |

OTHER PUBLICATIONS

Pathak, M.A. et al., Multiparty Differential Privacy via Aggregation of Locally Trained Classifiers, Advances in Neural Information Processing Systems 23, 2010, pp. 1876-1884, [online][retrieved from the Internet Jan. 4, 2016] <URL:http://machinelearning.wustl.edu/mipapers/papers/NIPS2010_0408>.

Liu, F. et al., Encrypted Gradient Descent Protocol for Outsourced Data Mining, 2015 IEEE 29$^{th}$ International Conference on Advanced Information Networking and Applications (AINA 2015), Proceedings of a meeting help Mar. 24-27, 2015, Gwangiu, South Korea, ISBN: 9781479979066, Print on Demand Publisher: Curran Associates, Inc. (Jul. 2015), pp. 339-346. [online][retrieved from the Internet Dec. 18, 2015] <URL:http://ieeexplore.ieee.org/xpl/articleDEtails.jsp?reload=true&narnumber=7097989&pumumber%3D7095453%26filter%3DAND(p_IS_Number%3A7097928)%26pageNumber%3D3>.

Chaudhuri, K. et al., Differentially Private Empirical Risk Minimization, Journal of Machine Learning Research 12 (2011), pp. 1069-1109.

Wan, L. et al., Privacy-Preservation for Gradient Descent Methods, Research Track Paper, pp. 775-783.

Wan, L. et al., Privacy-Preservation for Stochastic Gradient Descent Application to Secure Logistic Regression, The 27$^{th}$ Annual Conference of the Japanese Society for Artificial Intelligence, 2013, pp. 1-4.

Amirbekyan, A. et al., Privacy Preserving Regression Algorithms, School of ICT, Griffith University, Meadowbrook QLD 4131, Australia, 14 pages.

Sakuma, J., et al., Privacy-Preserving Evaluation of Generalization Error and Its Application to Model and Attribute Selection, Appears in *Proceedings of the 1$^{st}$ Asian Conference on machine Learning*, Nanjing, China, Nov. 2-4, 2009.

Duchi, J. et al., Privacy Aware Learning, Department of Electrical Engineering and Computer Science, Department of Statistics, University of California, Berkeley, CA.

Bhandare, S, Data Transformation and Encryption Based Privacy Preserving Data Mining System, International Journal of Advanced Research in Computer Science and Software Engineering, Department of Computer Science and Engineering, Khandwa (M.P.) India, pp. 366-369.

International Search Report and Written Opinion corresponding to PCT/AU2015/050661 dated Jan. 8, 2016.

\* cited by examiner

GRADIENTS OVER DISTRIBUTED DATASETS

CROSS-REFERENCE TO RELATED APPLICATIONS

The present application claims priority from Australian Provisional Patent Application No 2014904260 filed on 24 Oct. 2014, the content of which is incorporated herein by reference.

TECHNICAL FIELD

This disclosure relates to characterising data sets that are distributed as multiple data subsets over multiple computer systems.

BACKGROUND ART

Companies that provide services or products over the Internet often collect a wide range of data from their customers and process this data to obtain aggregated insights into their client's behaviour.

Figure 1:
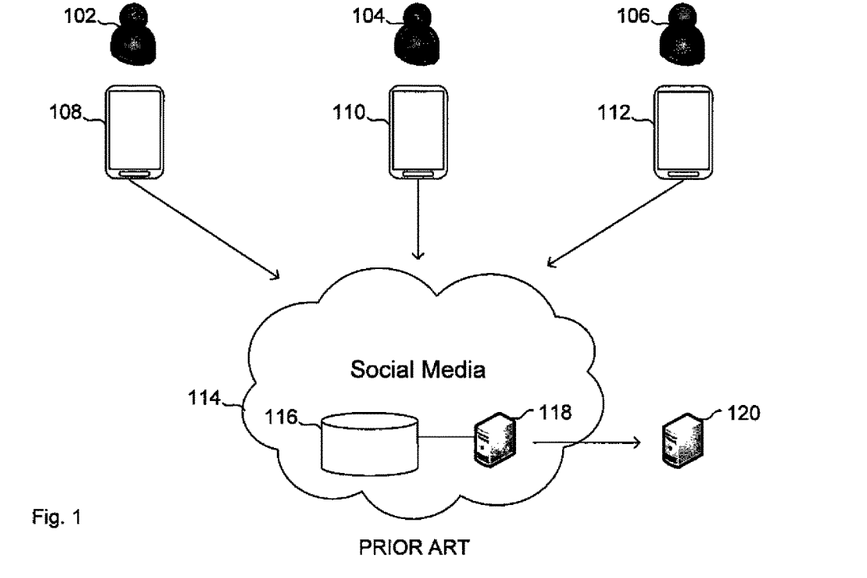
FIG. 1 illustrates a prior art corporate-centric computer network with a social media provider.

FIG. 1 illustrates a prior art corporate-centric computer network 100 with three participating customers or users 102, 104 and 106 operating three respective Internet enabled communication devices, such as smartphones, 108, 110 and 112. The users 102, 104 and 106 are registered with social media provider 114 and interact with each other by providing indications of their preferences, posting comments or uploading and tagging photos. In essence, these activities involve storing the personal data related to the three users 102, 104 and 106 on a database 116 operated by the social media provider 114.

Connected to the database 116 is a server 118 that analyses the user data stored on database 116 to derive aggregated information. The result may then be sold to a third party, such as an advertising company 120. However, users 102, 104 and 106 are reluctant to share private or sensitive information. Therefore, it is difficult to derive aggregated insights based on private or confidential data related to the users 102, 104 and 106.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

DISCLOSURE OF INVENTION

There is provided a method for determining a gradient of an objective function to iteratively characterise a data set that is distributed as multiple data subsets over multiple computer systems. The method comprises:
  determining by the a first computer system a partial gradient of the objective function over a first data subset stored on the first computer system;
  determining by the first computer system random data;
  determining by the first computer system an altered gradient by modifying the partial gradient based on the random data;
  encrypting by the first computer system the altered gradient to determine a first encrypted gradient such that one or more operations on the altered gradient can be performed based on the first encrypted gradient;
  determining by the first computer system an output gradient based on the first encrypted gradient;
  sending by the first computer system the output gradient to a receiving computer system.

Since the partial gradient is altered based on random data and encrypted it is difficult, if not impossible, for the second computer system to calculate the data that is stored on the first computer system. This is an advantage as it allows to preserve the privacy of the data stored on the first computer system while still allowing to characterise the data set.

The method may further comprise:
  receiving by the first computer system a second encrypted gradient of the objective function over a second data subset, the second data subset being stored on one or more second computer systems different to the first computer system;
wherein determining the output gradient comprises performing the one or more operations to combine the first encrypted gradient with the second encrypted gradient.

Since the first and second encrypted gradients are combined, many different computer systems can operate in a chain structure where the partial gradient is refined while it is passed through the chain and combined with the current local gradient at each computer system. Using the one or more operations allows the combination of the gradients without having to decrypt them. As a result, the partial gradients and the data remain confidential.

Performing the one or more operations to combine the first encrypted gradient with the second encrypted gradient may comprise adding the first encrypted gradient to the second encrypted gradient.

Determining random data may comprise determining a random number and determining the altered gradient may comprise multiplying the random number with the partial gradient or adding the random number to the partial gradient.

The method may further comprise:
  encrypting the random data to determine first encrypted random data;
  determining output random data based on the first encrypted random data; and
  sending the output random data to the receiving computer system.

The method may further comprise:
  receiving by the first computer system second encrypted random data;
  wherein determining the output random data comprises performing the one or more operations to combine the first encrypted random data with the second random data.

Determining the partial gradient may be based on a regression model.

The first data subset may comprise training data for training a classifier and the training data may comprise one or more samples and a label for each of the one or more samples. The one or more samples may comprise DNA related data.

Determining the partial gradient may comprise determining the partial gradient to extract principle components of the data set. The first data subset may comprise multiple images.

The first data subset may comprise training data of a recommender system and determining the partial gradient may comprise determining the partial gradient of the recommender system.

The data set may comprise data from which an anomaly or outlier is to be detected and determining the partial gradient may comprise determining the partial gradient of an anomaly or outlier detection system.

The first data subset or the second data subset or both may consist of a single data record.

Encrypting the altered gradient may comprise using Paiflier encryption.

Software, when installed on a computer, causes the computer to perform the above method.

There is provided a computer system for determining a gradient of an objective function to iteratively characterise a data set that is distributed as multiple data subsets over multiple computer systems. The computer system comprises:
 a datastore to store a first data subset;
 a processor to
  determine a partial gradient of the objective function over the first data subset,
  determine random data,
  determine an altered gradient by modifying the partial gradient based on the random data,
  encrypt the altered gradient to determine a first encrypted gradient such that one or more operations on the altered gradient can be performed based on the first encrypted gradient, and
  determine an output gradient based on the first encrypted gradient; and
 an output port to send the output gradient to a receiving computer system.

There is provided a method for updating a characterisation of a data set that is distributed as multiple data subsets over multiple computer systems. The method comprises:
 sending an initial characterisation of the data set to the multiple computer systems;
 receiving an encrypted gradient of an objective function over the data set;
 receiving encrypted random data;
 decrypting the encrypted gradient to determine a decrypted gradient;
 decrypting the encrypted random data to determine decrypted random data; and
 determining an updated characterisation of the data set based on the decrypted gradient and the decrypted random data.

Determining the updated characterisation may comprise partially reverting an alteration of the gradient based on the random data.

The characterisation may comprise one or more coefficients of a linear model.

Determining an updated characterisation may comprise adding the initial weights of the linear model to a fraction of the decrypted gradient over the decrypted random data multiplied by a learning factor.

Software, when installed on a computer, causes the computer to perform the above method for updating a characterisation of a data set.

There is provided a computer system for updating a characterisation of a data set that is distributed as multiple data subsets over multiple computer systems. The computer system comprises:
 a communication port to
  send an initial characterisation of the data set to the multiple computer systems,
  receive an encrypted gradient of an objective function over the data set, and
  receive encrypted random data; and
 a processor to
  decrypt the encrypted gradient to determine a decrypted gradient,
  decrypt the encrypted random data to determine decrypted random data, and
  determine an updated characterisation of the data set based on the decrypted gradient and the decrypted random data.

Optional features described of any aspect of method, computer readable medium or computer system, where appropriate, similarly apply to the other aspects also described here.

BRIEF DESCRIPTION OF DRAWINGS

An example will be described with reference to

BEST MODE FOR CARRYING OUT THE INVENTION

Figure 2:
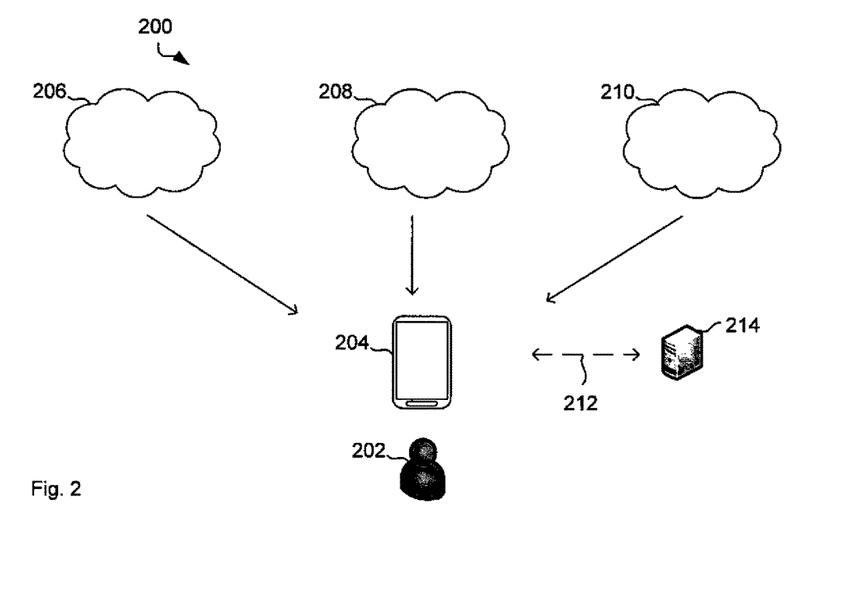
FIG. 2 illustrates a user-centric computer network with three service providers.

FIG. 2 illustrates a person-centric computer network 200 comprising user 202 operating a communication device, such as a smartphone or tablet computer, 204. User 202 receives products or services from providers 206, 208 and 210. The service providers 206, 208 and 210 collect data that is related to that user 202 arid provide that data back to the user 202 to be stored on communication device 204. As a result, communication device 204 holds a rich collection of personal data related to user 202. Of course, this data may comprise data that is generated by user 202, such as by the user 202 providing preferences, taking photos, answering questions or providing comments. It is also possible that the data is stored on a cloud service and the phone provides a key, such as through a user interface, to grant the right to run some computation over that data stored in the cloud.

User device 204 and multiple further user devices (not shown) are connected 212 to an aggregating system 214. Although the aggregating system 214 is shown as a single computer, the aggregating system can comprise multiple nodes, some of which may include those holding data (such as the user's smartphone 204). The connection 212, that is the communication, between the user device 204 and the aggregating system 214 is such that the aggregating system 214 can determine or learn aggregated data, but the used data stored on user device 204 is not shared with aggregating system 214.

As a result, an individual 202 gathers and aggregates data from all the companies 206, 208 and 210 with whom they engage, enabling deep insights from all their engagements and consequently a much more personal understanding of individual needs, wants and behaviour.

This architecture 200 has a number of consequences. Most important, individuals now aggregate their own data and can provide informed consent as to its use. First, this means that privacy becomes a local people-centric issue and not a matter of how companies or organisations share their data. This turns the whole privacy debate on its head. Second, enormously rich data about individual behaviour becomes available at a single location. Such rich data can be aggregated by the individual as organisations themselves will not and often cannot share this deep information. Such rich data enables much deeper insights into individual behaviour and drives a new personalised analytics paradigm.

One important application of this technology is in management of personal health. Individuals can own their own personal health information and individuals can aggregate this information locally on their devices to provide the best possible health predictions and management solutions.

The health information may include the individual (differential) genomic sequence, the personal phenotype, information ingested during visits to the doctors or hospital, and personal (food and activity) life-style information collected from the device itself or ingested from the now popular activity measurement devices such as FuelBand.

There are three example use-cases for health-related applications: A visit to the doctors and the consequent prescription of a specific drug; a medical researcher seeking to run cohort studies across a population; and an individual who wants to receive the best advice, targeted at their personal needs, sourced from the world-best medical practitioners.

Figures 3A, 3B:
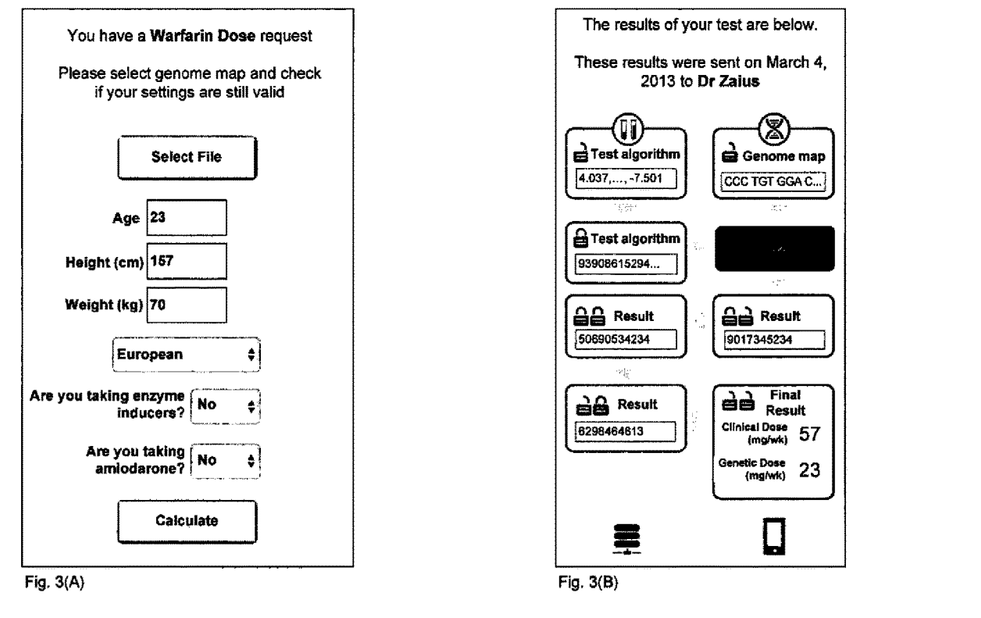
FIGS. 3a and 3b illustrate screenshots of a mobile app to calculate a dosage of a drug.

FIGS. 3a and 3b illustrate two screen shots from a Warfarin dose smartphone application. FIG. 3a shows the individual's genome and phenotype information while FIG. 3b shows the results of the secure computation of Warfarin dose.

In this scenario, an individual's genome and phenotype are held securely and privately on a mobile phone. The doctor wishes to determine the appropriate dosage of Warfarin (a blood thinning agent whose optimal dosage depends on both genetic and phenotype information). A dosage is computed and returned to the doctor. While private personal data is used to compute the correct dosage, this information is kept secure by the individual and not provided to either the doctor or the drug company.

Another health related scenario is to provide a tool for cancer researchers to query individually held genomic information. Population genetics has the potential to have a major impact on understanding cancer and the development of cancer therapies—and will become increasingly important as the cost of whole genome sequencing drops to below $1,000. However, access to genomic databases has proved to be enormously difficult as different institutions have access to different data and as ethical and institutional constraints prevent this data being shared, particularly across international borders. This has become a huge impediment to cancer research.

In one scenario, all individuals own their own genetic information maintained on a personal device or on a personal cloud. Individuals then volunteer to participate with their devices while being confident that the computation is kept secure and that the data is kept private and the results anonymous.

In health-related applications, it is possible for researchers to ask questions, such as how many people have this combination of SNPs, are between these weights, have taken this medication in the past six months and exercise more than twice a week? Provided is a solution to the problem of ethics and data privacy, while simultaneously providing richer and more personal information for researchers.

Many of the privacy, security and data richness issues that abound in health are equally important in banking and personal finance applications. Decisions about spending and investment, risk and insurance, short versus long term behaviour are important both to the individual and the financial institution concerned. A solution is provided to both the data aggregation and data privacy issues while enabling rich new capabilities with analytics applied to individual customers.

In a first example, individuals aggregate data and financial institutions want to better target, predict and personalise financial products and advice. In a second example businesses and even business divisions want to undertake analytics or share information across a number of different databases while making guarantees about the security and privacy of each individual database.

Individuals have access not only to their personal financial information, but also direct access to their life style, family circumstance, social behaviour, spending and investment profiles with third parties. The proposed solution allows aggregation of this personal data to create a rich source of information at a single location, while still allowing insights to be generated from the data. Further, a financial institution can use this information to provide far more directed financial advice and personal product direction. This ensures the privacy and security of information for the individual while enabling directed individual and personalised analyses.

It is also possible to envisage a wide range of potential commercial applications, allowing individuals to monetise their data by selling deeper individual insights to third party organisations (media, marketing, sales and others).

Figure 4:
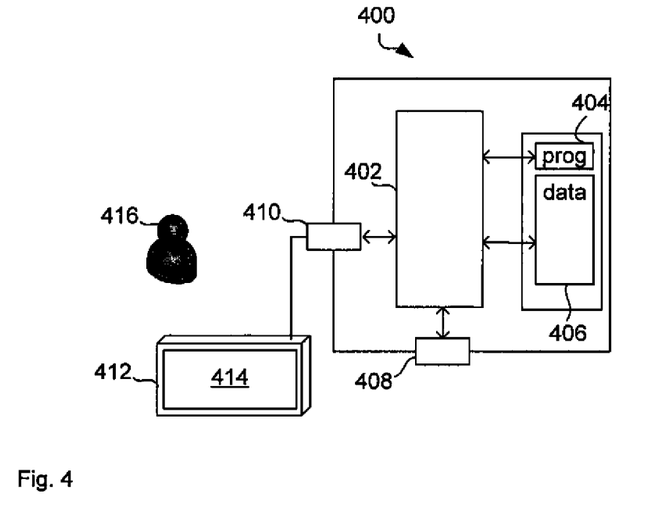
FIG. 4 illustrates a computer system for determining a gradient of an objective function.

FIG. 4 illustrates a computer system 400 for determining a gradient of an objective function. The computer system 400 may be a mobile phone and comprises a processor 402 connected to a program memory 404, a data memory 406, a communication port 408 and a user port 410. The program memory 404 is a non-transitory computer readable medium, such as a hard drive, a solid state disk or CD-ROM. Software, that is, an executable program stored on program memory 404 causes the processor 402 to perform the method in FIG. 5, that is, processor 402 determines a partial gradient of the local data, randomizes and encrypts the gradient before sending the output gradient to a receiving computer system.

Since this disclosure describes multiple computer systems with similar elements to computer system 400, computer system 400 is described and illustrated only once. Where the following description states that a particular device, such as a smartphone or server performs a particular step, it is to be understood that this step is performed by processor 402 of that particular smartphone or server.

The term "determining a partial gradient" refers to calculating a value that is indicative of the partial gradient. This also applies to related terms. The objective function may be a cost function, such as an error function between a linear regression model and the dataset, an error function between a set of principle components and the dataset or any other cost function that expresses how well the dataset is characterised. Principle components are used in principle component analysis (PCA). The principle components are the most significant basis vectors in the dataset, which means that a linear combination of the principle components approximates the dataset. For example, a principle component of 1000 face images with 200×300 pixels is also a 200×300 pixel image and represents the most common face features.

It is noted that the gradient of the objective function can be determined without explicitly referring to the objective function itself. Examples below show how a closed form expression can be used to determine the gradient of the objective function directly from predictions and the values of the data set without calculating the objective function for the values of the data set.

The processor 402 may then store the output gradient on data store 406, such as on RAM or a processor register. Processor 402 may also send the determined randomised and encrypted output gradient via communication port 408 to another computer system, such as another mobile phone.

The processor 402 may receive data, such as data of a data set to be characterised, from data memory 406 as well as from the communications port 408 and the user port 410, which is connected to a display 412 that shows a visual representation 414 of the data set or characterisation of the data set to a user 416. In one example, the processor 402 receives the data set from a storage device via communications port 408, such as by using a Wi-Fi network according to IEEE 802.11. The Wi-Fi network may be a decentralised ad-hoc network, such that no dedicated management infrastructure, such as a router, is required or a centralised network with a router or access point managing the network.

In one example, the processor 402 receives and processes the data set in real time. This means that the processor 402 determines the output gradient every time new data of the data set is received and completes this calculation before the next data update is provided.

For example, the aim may be to determine the principle components of a data set comprised of photographs of faces and to characterise the data set in terms of those principal components, also called eigenfaces, to compress the face images. Processor 402 determines a partial gradient based on the face images that are stored locally. An aggregating computer system then determines based on output gradients from multiple computer systems a final gradient and optimises a cost function to determine the principle components of the data set. The aggregating computer then sends these principal components back to the computer systems, which in turn, use the principal components to store linear combination of principal components instead of the image files.

Although communications port 408 and user port 410 are shown as distinct entities, it is to be understood that any kind of data port may be used to receive data, such as a network connection, a memory interface, a pin of the chip package of processor 402, or logical ports, such as IP sockets or parameters of functions stored on program memory 404 and executed by processor 402. These parameters may be stored on data memory 406 and may be handled by-value or by-reference, that is, as a pointer, in the source code.

The processor 402 may receive data through all these interfaces, which includes memory access of volatile memory, such as cache or RAM, or non-volatile memory, such as an optical disk drive, hard disk drive, storage server or cloud storage. The computer system 400 may further be implemented within a cloud computing environment, such as a managed group of interconnected servers hosting a dynamic number of virtual machines.

It is to be understood that any receiving step may be preceded by the processor 402 determining or computing the data that is later received. For example, the processor 402 determines the partial gradient and stores the partial gradient in data memory 406, such as RAM or a processor register. The processor 402 then requests the data from the data memory 406, such as by providing a read signal together with a memory address. The data memory 406 provides the data as a voltage signal on a physical bit line and the processor 402 receives the partial gradient via a memory interface.

Figure 5:
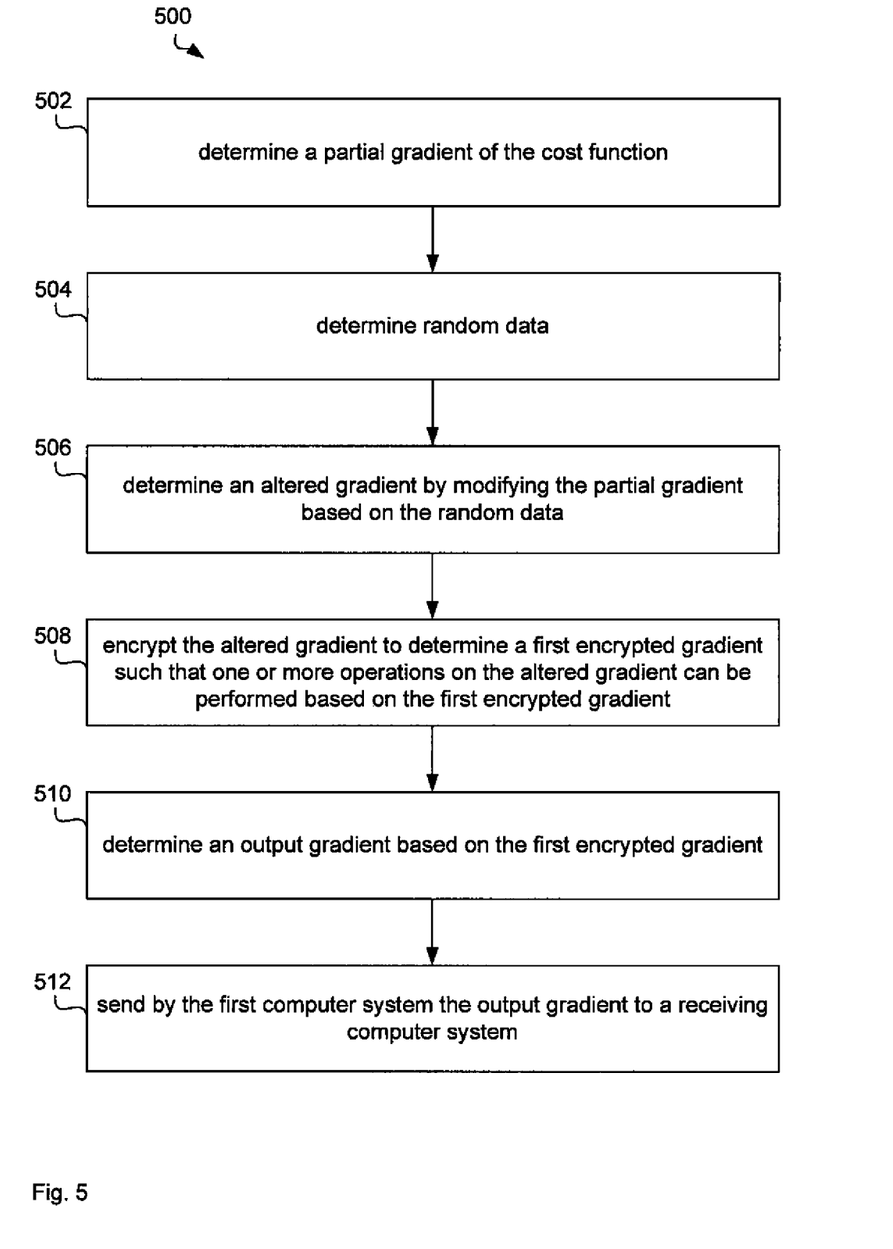
FIG. 5 illustrates a method for determining a gradient of an objective function.

FIG. 5 illustrates a method 500 as performed by processor 402 for determining a gradient of a objective function to iteratively characterise a data set. that is distributed as multiple data subsets over multiple computer systems.

Figure 6A:
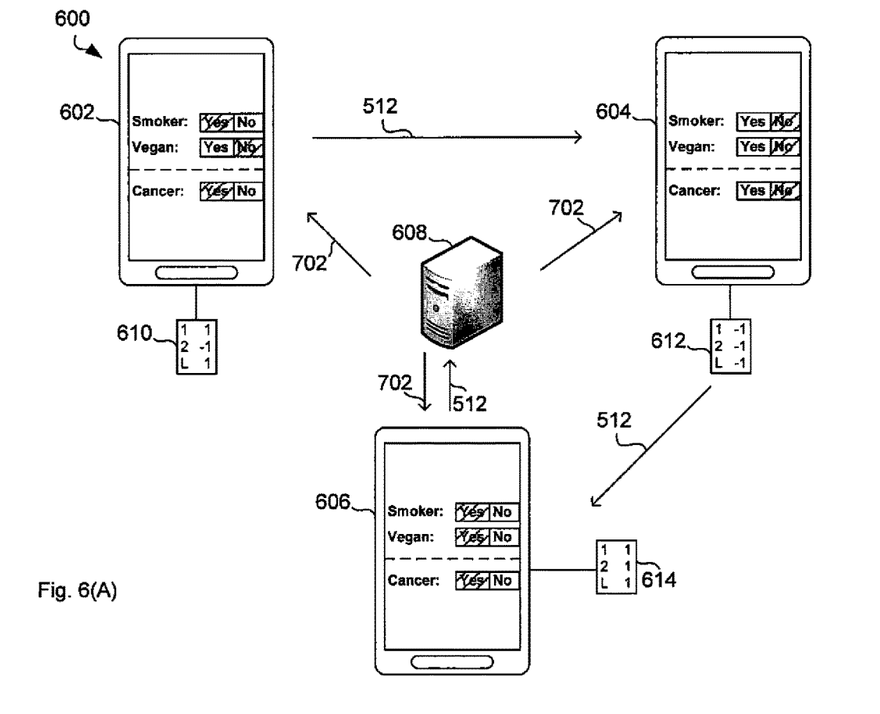
FIGS. 6a and 6b illustrate examples of computer networks with a distributed data set.

FIG. 6a illustrates a computer network 600 comprising multiple computer systems. In particular, FIG. 6a shows a first computer system 602, a second computer system 604, a third computer system 606 and a central learning server 608. Each of the three computer systems 602, 604 and 606 and the central learning server 608 comprise the elements described with reference to FIG. 4.

In one example, the aim is to learn a predictive model—such as logistic regression with a regulariser. This involves finding the parameter vector $\theta^*$ that minimises the objective function $$L(\theta)=\Sigma_{i=1}^{N}\Sigma_{j=1}^{N_i}\log(1+\exp(-y_{ij}\theta^T x_{ij}))+\lambda\theta^T\theta\Sigma_{i=1}^{N}N_i$$

where N is the number of data providers, $N_i$ is the number of examples held by data provider i, $x_{ij}$ is the jth feature vector held by data provider i, $y_{ij}$ is a binary label corresponding to the feature vector $x_{ij}$, and $\lambda$ is the regularisation parameter. We aim to find $\theta^*$, or a nearby parameter vector, while maintaining the privacy of the training examples ($x_{ij}$, $y_{ij}$). It is noted that training examples may equally be denoted as ($d_i$, $t_i$) in other examples below.

One procedure for finding the optimal parameter vector involves iteratively improving an initial guess $\theta_1$ using a gradient descent algorithm. Each iteration begins with the data providers calculating the gradient for their portion of the objective function. These gradients are sent to a central learner who sums the local gradients and the gradient of the regulariser $\lambda\theta^T\theta\Sigma_i N_i$ to obtain the global gradient. The learner subsequently updates the parameters according to the gradient and a step size. Finally, the updated parameters are communicated to each of the nodes.

Procedures of this type are not privacy preserving due to the transmission of the local gradients directly to the learner. By manipulating the parameter vector the learner can use these gradients to obtain information about the data sets. This is particularly problematic when the size of the data sets held by a data provider is small.

To account for these failings, the proposed solution augments a gradient descent algorithm with a procedure involving random sampling, partial homomorphic encryption, and aggregation so as to obscure the local gradients from the learner and thus ensure the privacy of the data. Before the gradient descent begins, the learner provisions several aggregating nodes. These nodes may also be data providers. The learner also generates a public/private key pair for an additively homomorphic cryptosystem, such as the Paillier cryptosystem, and sends the public key to each of the data providers.

In this example, the task is to determine a logistic regression classifier based on a simple questionnaire. The questionnaire comprises three questions. Two questions are related to features while the third question is related to a label. The first question is whether a person is a smoker, while the second question is whether the person is a vegan. The third question is whether the person has cancer, that is, the label for each samples is whether the person has 'cancer'.

The task is to construct a classifier that can predict whether a person has cancer based on whether they are a smoker or a vegan. However, having cancer is information that most users would not want to share openly and therefore, it is important for the questionnaire to be successful that the privacy is preserved, which means that the information whether a particular user has cancer is not disclosed to any party or device other than computer system 602 for the first user.

In this example, the three computer system 602, 604 and 606 are smartphones and the questionnaire questions are displayed on the respective screens. A user of the first smartphone 602 has answered 'Yes' to being a smoker, 'No' to being a vegan and 'Yes' to having cancer. The answers are stored as a first data subset 610 stored on the data memory (referred to as 406 in FIG. 4) of first computer system 602. The first row relates to feature '1', which is 'smoker', the second row relates to feature '2', which is 'vegan' and the third row relates to the label 'L', which is 'cancer'. In this example, the second column stores the feature value of the respective feature where '1' represents a 'yes' answer and '−1' represents a 'no' answer.

Based on the results provided to the first smartphone 602, it appears that smoking and not being a vegan leads to having cancer. However, this conclusion is based on a single sample and is therefore statistically not significant. Incorporating more participants would make the result more significant.

In a similar way, a user of the second smartphone 604 has indicated that he is not a smoker, is not a vegan and has no cancer, which is stored as second data subset 612 on second computer system 604. A user of the third smartphone 606 has indicated that she is a smoker, a vegan and has cancer, which is stored as third data subset 614 on third computer system 606.

In other examples, the training data, that is, the data subsets 610, 612 and 614 may store other types of data, such as face images as described above or a genome and a particular disease. For example, the data subsets 610, 612 and 614 may include one feature for each of a large number of single-nucleotide polymorphism (SNPs), such that the subset stores a '1' if that person's DNA shows that SNP or a '−1' if it doesn't. The label may again be a specific disease, such as diabetes.

In another example, the data subsets 610, 612 and 614 comprise features related to user data, such as age, gender, address, nationality, ethnicity and so on. This user data should not be disclosed or shared with other parties.

The label may represent historical behaviour data of the respective users, such as purchased items, watched movies, read books or individual words of comments, website keywords or photographs that the users have indicated as their preference, such as by selecting a 'like' or 'love it' link.

The network 600 can then function as a recommender system where characterising the dataset means learning the relationship between the historical behaviour, preferences of the users and user data. As a result, additional items, movies, books, comments, websites photographs or the like can be recommended to the user according to the user data or preferences.

Although the data subsets 610, 612 and 614 in the above examples only comprise a single sample, it is to be understood that each data subset may equally have more than one sample and each sample may have more than one label. In the multi-label example, the processes described herein are simply performed for each of the multiple labels separately.

Figure 6B:
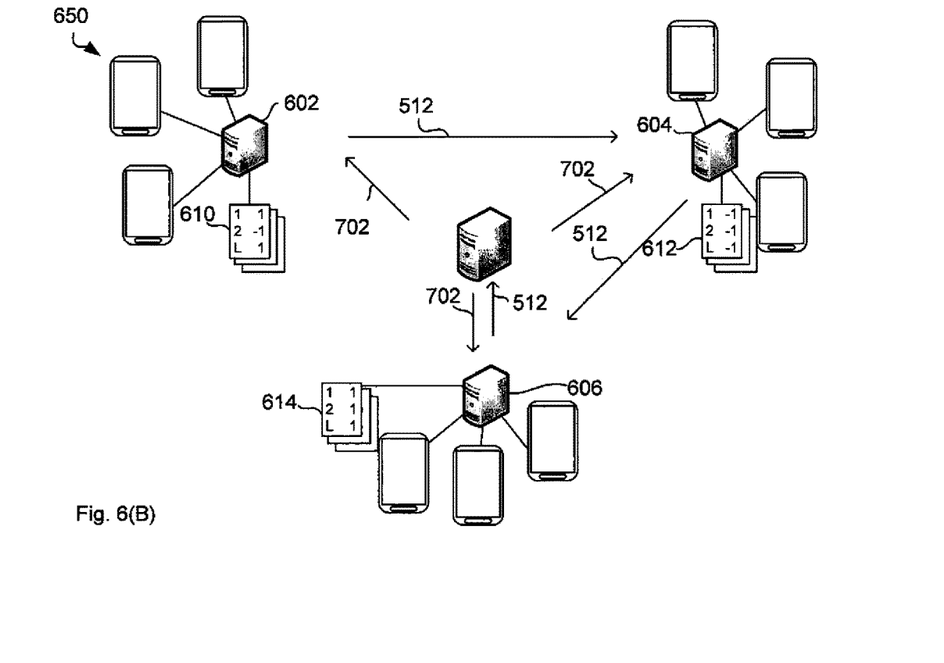

FIG. 6b illustrates another example of a computer network 650 where smartphones or any other personal computing devices act as access points to the data while the data is stored on three servers 602, 604 and 606. The same reference numerals are used in FIG. 6a and FIG. 6b to denote that elements with the same reference numerals perform the same functions. The three servers 602, 604 and 606 in FIG. 6b may be operated by three respective companies and they provide the encrypted gradient updates based on their data as will be described below with reference to FIG. 6a.

Referring back to FIG. 5, processor 402 of the first computer system 602 determines 502 a partial gradient g of the objective function over the first data subset 610 stored on the first computer system 602. Determining the partial gradient may be based on a regression model, which means the partial gradient is computed such that it points towards a reduction in the fitting error of the regression model.

The data subset may be written as $\{(d_i, t_i)\}$, where $d_i$ is a vector comprising the feature values, such as the first two rows of the second column of data subset 610 in FIG. 6a and $t_i$ is the label in the third row of the second column of the data subset 610. The partial gradient may be based on current model parameters $\Theta$ which may be provided by the learning server 608. In the first iteration when no model parameters are available from a previous iteration, all model parameters may be initialised to zero.

The number of model parameters may be identical to the number of feature values, that is, two in this example, such that processor 402 can calculate predictions y of the label $t_i$ ('cancer') based on the feature values ('smoker' and 'vegan') $d_i$ by calculating $y_i = \sigma(\Theta^T d_i) = 1/(1+\exp(-\Theta^T d_i))$. For the example of the first computing device and assuming zero model parameters, the predicted label y for the first data subset, that is feature values '1' and '−1' is $y_i = 1/(1+\exp(-(0.1+0\cdot(-1)))) = 1/(1+\exp(0)) = \frac{1}{2}$, which means that the prediction is exactly in the middle between having cancer and not having cancer.

The error between a prediction $y_i$ and the actual label $t_i$ can then be expressed in terms of a loss function $l(y_i, t_i) = t_i \ln y_i + (1-t_i) \ln(1-y_i)$. For the single example described above, the result of the loss function is $l(\frac{1}{2}, 1) = 1 \cdot \ln \frac{1}{2} + 0 \cdot \ln \frac{1}{2} = \ln \frac{1}{2}$. The partial gradient of the loss function applied to this example is given by $$\partial l(y_i, t_i)/\partial \Theta_i = (y_i - t_i) d_i = (0.5 - 1) \begin{bmatrix} 1 \\ -1 \end{bmatrix} = \begin{bmatrix} -0.5 \\ 0.5 \end{bmatrix}.$$

It is noted that the shorthand $\partial l(y_i, t_i)$ is used below in place of $\partial l(y_i, t_i)/\partial \Theta_1$.

The objective function for the entire dataset is simply the sum of the loss functions applied to each example $L(\Theta) = \Sigma_i l(y_i, t_i)$ where we note that each prediction $y_i$ is implicitly dependent on the parameters $\Theta$ as defined above. Similarly, the partial gradient of the objective function with respect to the parameters is simply the sum of the partial gradients of the loss functions $\partial L(\Theta)/\partial \Theta = \Sigma_i \partial l(y_i, t_i)$.

Processor 402 can update the model parameters by $\Theta \Leftarrow \Theta - \eta \partial l(y_i, t_i)$ and in this case assuming $\eta = 1$:

$$\Theta \leftarrow \begin{bmatrix} 0 \\ 0 \end{bmatrix} - \begin{bmatrix} -0.5 \\ 0.5 \end{bmatrix} = \begin{bmatrix} 0.5 \\ -0.5 \end{bmatrix}.$$

This shows that now the answer to 'smoker' has a positive contribution to 'cancer' and the answer to 'vegan' has a negative influence on 'cancer', which corresponds to the intuitive result above.

Since the updated model parameters are based on only a single sample, processor 402 of first smartphone 602 should send the partial gradient to the second smartphone 604 to allow the second smartphone 604 to update the partial gradient based on the second data subset 612. However, sending the partial gradient in plain text, that is, $$\begin{bmatrix} -0.5 \\ 0.5 \end{bmatrix}$$

would allow the second smartphone 604 to reconstruct the first data subset 610 or at least derive some information about the first data subset 610.

Therefore, processor 402 determines 504 random data, such as a vector of random numbers with the same dimension as the number of features $a_i \in (0,1)^n$. For example, the random data may be $$\begin{bmatrix} 0 \\ 1 \end{bmatrix}.$$

Processor 402 then determines 506 an altered gradient by modifying the partial gradient based on the random data, such as by computing $a_i \otimes \partial l(y_i, t_i)$, where $\otimes$ denotes element-wise multiplication. In other examples, $\otimes$ may denote element-wise addition. In the current example of element-wise multiplication, the result is $$\begin{bmatrix} 0 \\ 0.5 \end{bmatrix}.$$

The example above is given for illustrative purpose only. Due to the small number of features, it may be preferred that first smartphone 602 does not send the output gradient to the second smartphone 604 but to a trusted aggregator, which performs the Paillier addition. This will be explained in more detail with reference to FIG. 8.

In another example, the data provider, that is one of the smartphones, samples a vector $g_i$ from the uniform distribution with maximal values according to $\partial l(y_i, t_i)$. That is, the jth component of $g_i$ is uniformly sampled from the interval $[0, \partial_j l(y_i, t_i)]$ where $\partial_j l(y_i, t_i)$ denotes the jth component of the gradient $\partial l(y_i, t_i)$. The data provider then calculates a normalisation factor $r_i$, whose jth component is given by $\partial_j l(y_i, t_i)/g_{ij}$ so that $r_{ij} g_{ij} = \partial_j l(y_i, t_i)$. This normalisation factor will be used subsequently by the learner to diminish the detrimental effects of the randomly sampled gradient. The randomised gradient and normalisation factor are then encrypted with the learner's public key and sent to an aggregating node.

After that, processor 402 encrypts 508 the altered gradient to determine a first encrypted gradient by calculating $E(a_i \otimes \partial l(y_i, t_i))$, where $E( )$ is an encryption function. The encryption function is such that one or more operations on the altered gradient $a_i \otimes \partial l(y_i, t_i)$ can be performed based on the encrypted gradient $E(a_i \otimes \partial l(y_i, t_i))$. An example of such an encryption is Paillier encryption, which will be described now.

Paillier encryption is based on an asymmetric key pair generated by the following procedure. Two large primes p, q are chosen randomly such that the greatest common divisor of pq and (p−1)(q−1) is 1. Then, the integer n=pq and the least common multiple $\lambda$=lcm(p−1, q−1) of p−1 and q−1 are computed. Subsequently, a random integer $g \in \mathbb{Z}_{n^2}$ is chosen from the multiplicative group of integers modulo $n^2$ such that n divides the order of g. This divisibility can be determined by checking for the existence of the modular multiplicative inverse $\mu = (L(g^\lambda \bmod n^2))^{-1}$ where $L(u) = (u-1)/n$. The result of this procedure is a public key given by (n, g) and a private key given by ($\lambda$, $\mu$).

The encryption of an integer message $m \in \mathbb{Z}^*_n$ is described by the function $E(m) = g^m r^n \bmod n^2$ where $r \in \mathbb{Z}^*_n$ is the multiplicative group of integers modulo n and is chosen at random. Decryption or an integer $c \in \mathbb{Z}^*_{n^2}$ is performed by the function $D(c) = \mu L(c^\lambda \bmod n^2) \bmod n$. These functions satisfy the property that $D(E(m))=m$, which is to say that an encrypted message can be decrypted to obtain the original message. The encryption function can be applied by any party who possesses the public key (n, g) while the decryption function can only be performed by a party who also knows the private key ($\lambda$, $\mu$).

In order to securely communicate using the Paillier cryptosystem, a first party generates a public/private key pair and publishes its public key. A second party can then obtain the public key of the first party and use it to encrypt a message before sending it to the first party. The first party can use its private key to decrypt the message. Provided that the first party keeps its private key a secret, any eavesdroppers will be unable to recover the original message.

The second important property of the Paillier cryptosystem is that one or more operations on the original data can be performed based on the encrypted data and in particular that multiplication of two encrypted messages is equivalent to the addition of the unencrypted messages modulo n. More formally, $D(E(m_1) \cdot E(m_2) \bmod n^2) = m_1 + m_2 \bmod n$ for any two messages $m_1, m_2 \in \mathbb{Z}^*_n$ encrypted with the same public key pair. One consequence of this property is that exponentiation of an encrypted number by an unencrypted number is equivalent to the multiplication of the two unencrypted numbers modulo n. That is, $D(E(m_1)^{m_2} \bmod n^2) = m_1 m_2 \bmod n$. These properties constitute an additive homomorphism and the Paillier cryptosystem is referred to as being additively homomorphic or partially homomorphic. A fully homomorphic encryption scheme also allows multiplication of two encrypted values.

In one example, homomorphism is a synonym for the property that addition and multiplication are allowed. In other examples, there may be other encryption methods which allow addition and multiplication and potentially other operations to be performed on the secret data based on the encrypted data without being considered homomorphic in a mathematically strict sense. For example, the operations based on the encrypted data may introduce some inaccuracy but that inaccuracy is acceptable as it introduces only a small amount of error into the final characterisation of the data set.

The Paillier cryptosystem allows the addition of integers. In order to sum floating point numbers they may be encoded as fixed point numbers. For example: 0.01 could be encoded as 10 with the respect to the base $10^{-3}$.

In this example, after modifying the partial gradient as explained above based on the random data, the processor 402 encrypts with the learner's public key the product of the random data with the partial gradient.

Then, processor 402 determines 510 an output gradient based on the encrypted gradient. In the case of the first smartphone 602, the output gradient is identical to the encrypted gradient and the determining step 510 is performed simultaneously with the previous step of encrypting the partial gradient.

Finally, the processor 402 sends 512 the output gradient to the second smartphone 604 using communication port 408. Since the output gradient is an encrypted randomised version of the partial gradient it is difficult, if not impossible for the second smartphone 604 to determine the first data subset 610 or derive any knowledge about the first data subset 610.

The second smartphone 604 also performs method 500 based on the second data subset 612. However, at any time before the step of determining the output gradient 510 the second smartphone 604 receives from the first smartphone 602 the output gradient determined by the first smartphone 602, which is in essence the encrypted gradient determined in step 508 over the first data subset 610. As shown in FIG. 6*a*, the first data set 610 is stored on smartphone 602 that is different to the smartphone 604 which is now performing the method 600.

In case of second smartphone 604, determining the output gradient in step 510 comprises performing the one or more operations to combine the encrypted gradient determined by second smartphone 604 with the encrypted gradient determined by first smartphone 604. In the example of using Paillier encryption, performing the one or more operations comprises performing an addition.

More formally, first smartphone 602 determines partial gradient $g^1_k$, multiplies the partial gradient with random number a, encrypts the result to obtain $E(ag^1_k)$ and sends $E(ag^1_k)$ to the second smartphone 604 over the internet using a 4G, LTE or Wifi connection, for example.

The second smartphone 604 receives the encrypted randomised partial gradient $E(ag^1_k)$ and determines partial gradient $g^2_k$, multiplies the partial gradient with random number b and encrypts the result to obtain $E(bg^2_k)$. The second smartphone 604 then combines the two encrypted randomised partial gradients by adding them to determine the output gradient in step 510. The encryption method allows the addition of the secret data based on the encrypted data, which means that adding the encrypted values is equal to adding the unencrypted values and then encrypting the result: $E(ag^1_k)+E(bg^2_k)=E(ag^1_k+bg^2_k)$.

Second smartphone 604 sends the result $E(ag^1_k+bg^2_k)$ to third smartphone 606 which similarly computes a further partial gradient over the third data subset 614, multiplies the partial gradient with random number c, encrypts the result, combines the encrypted gradient with the gradient received from second smartphone 604 and sends $E(ag^1_k+bg^2_k+cg^3_k)$ to the central server 608.

In one example, each of the three smartphones 602, 604 and 606 further encrypt their random number a, b and c, respectively. First smartphone 602 then sends the encrypted random number E(a) to second smartphone 604. Second smartphone 604 again performs the operations provided by the Paillier encryption to combine the received encrypted random number with the locally encrypted random number. That is, second smartphone 606 adds its own encrypted random number to obtain E(a+b) and sends this result to third smartphone 606 that similarly determines E(a+b+c) and sends this result to the server 608.

In the example above, the second smartphone 604 and the third smartphone 606 perform the homomorphic addition. However, it is equally possible in other examples that additional aggregators are present in the network 600.

Figure 8:
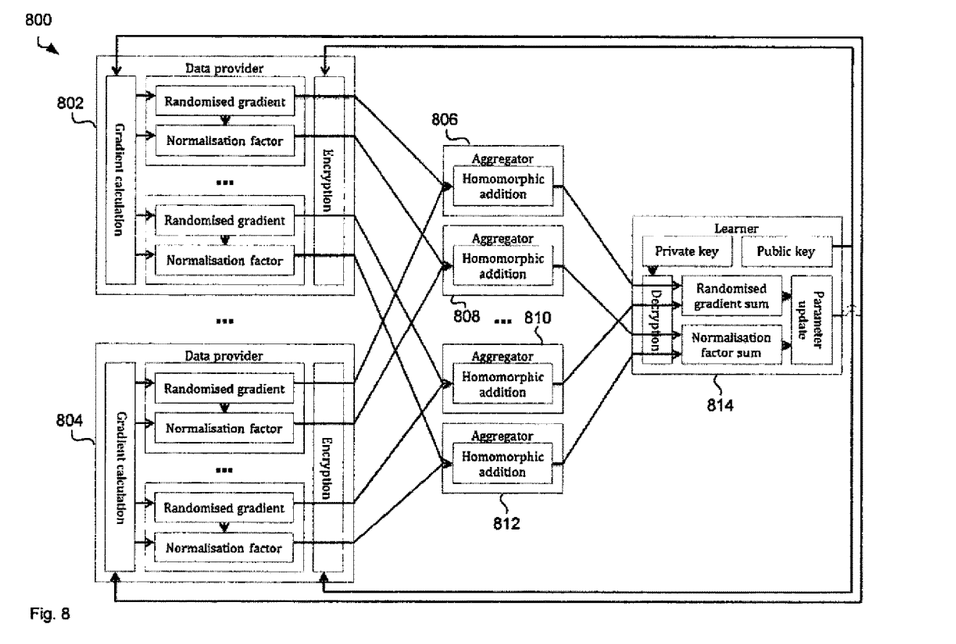
FIG. 8 illustrates an example of a network comprising multiple aggregators.

FIG. 8 illustrates another example of a network 800 comprising multiple data providers, two of which are shown as data providers 802 and 804. The data providers are connected to multiple aggregators, four of which are shown as aggregators 806, 808, 810 and 812 and a learner 814. The data providers can generate one or more randomised gradients and random numbers from the partial gradient and send these to the aggregators. The aggregators then add them as described above and send the results to the server 608.

Figure 9:
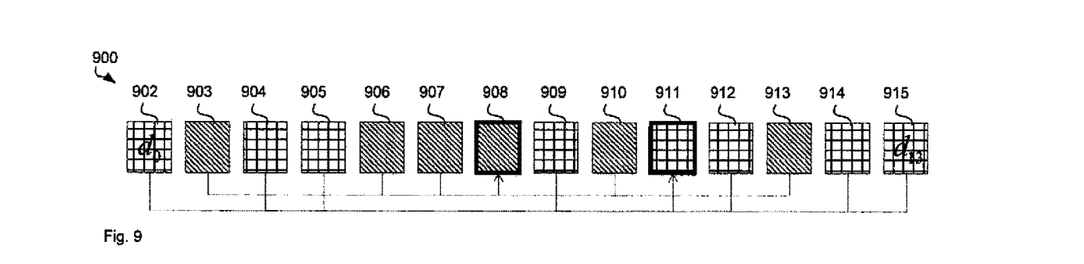
FIG. 9 illustrates another example of a network comprising multiple aggregators.

FIG. 9 illustrates yet another example of a network 900 comprising 14 nodes 902 to 915. Nodes 902, 904, 905, 909, 911, 912, 914 and 915 determine their respective encrypted gradients and send them together with the encrypted random numbers to a first aggregating node 911. The remaining nodes 903, 906, 907, 908, 910 and 913 also determine their respective encrypted gradients and send them together with the encrypted random numbers to a second aggregating node 911. The aggregating nodes 908 and 911 perform the Paillier addition and send the result to a learner server (not shown in FIG. 9).

In this example, all encryptions E( ) are performed using a public key, which means that any computer including the three smartphones 602, 604 and 606 can perform the encryption. However, only the central server 608 has the corresponding private key, which means that no computer other than the central server 608 can decrypt the encrypted data. Even the smartphones 602, 604 and 606 cannot decrypt the data that they have encrypted themselves.

Central server 608 has similar components to the three smartphones 602, 604 and 606 and the description of computer system 400 with reference to FIG. 4 also applies to the central server 608. Program memory 404 of server 608 has installed a software program, that causes the processor 402 to perform the method of FIG. 7.

Figure 7:
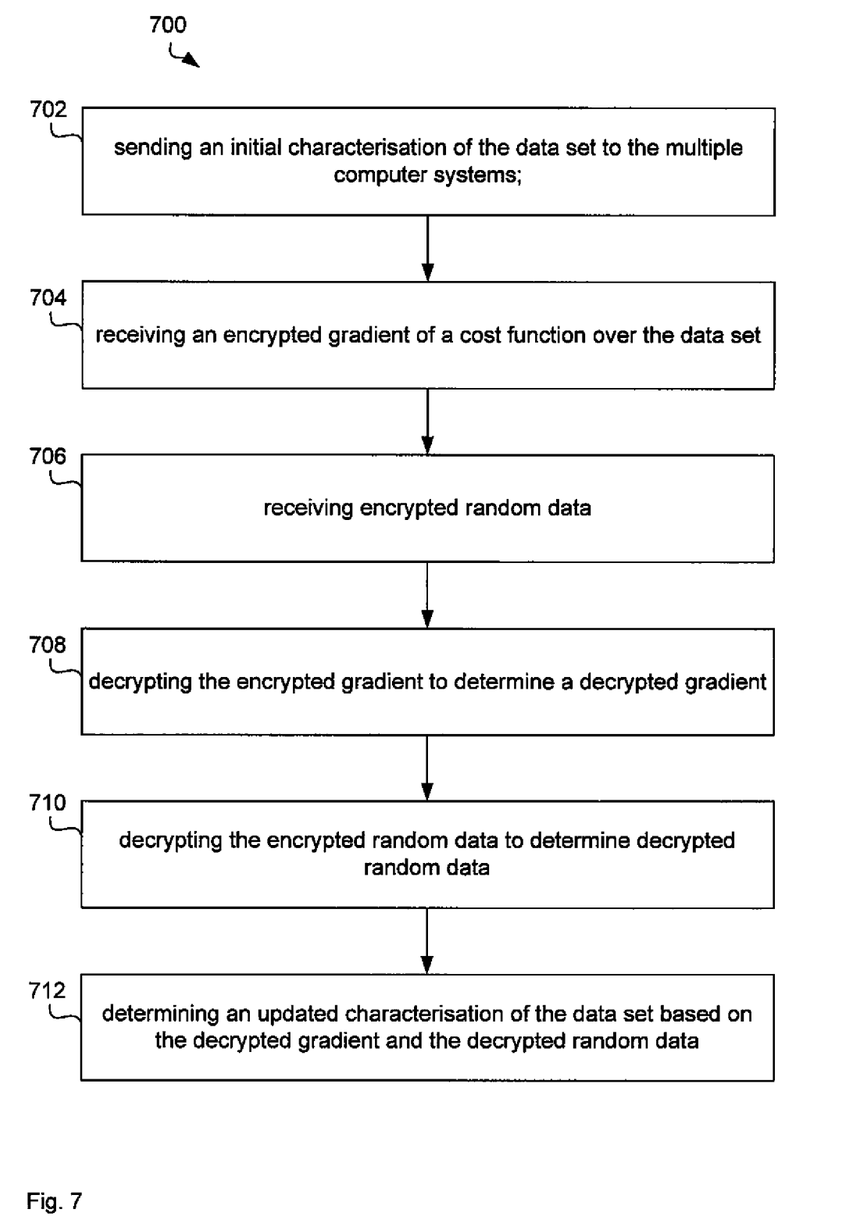
FIG. 7 illustrates a method for updating a characterisation of a data set.

FIG. 7 illustrates a method as performed by server 608 for updating a characterisation of a data set. As explained above, the dataset is distributed as multiple data subsets over multiple computer systems, such as three data subsets 610, 612 and 614 distributed over three smartphones 602, 604 and 606, respectively.

In order to initialise the smartphones 602, 604 and 606, server 608 uses communication port 408 of server 608 to send 702 an initial characterisation of the data set to the three smartphones 602, 604 and 606. In one example, server 608 sends the initial characterisation only to first smartphone 602 and the first smartphone 602 forwards the initial characterisation to the second smartphone 604 together with or separately from the encrypted gradient as described above.

Once the computation of partial gradients is completed as described above, server 608 receives 704 via the communication port 408 of server 608 the encrypted gradient $E(ag^1_k+bg^2_k+cg^3_k)$ of the objective function over the data set and receives 706 via the communication port 408 of server 608 the encrypted random data E(a+b+c). Server 608 then decrypts 708 the encrypted gradient $E(ag^1_k+bg^2_k+cg^3_k)$ to determine the decrypted gradient $ag^1_k+bg^2_k+cg^3_k$ and decrypts 710 the encrypted random data E(a+b+c) to determine decrypted random data a+b+c. Finally, server 608 determines 712 an updated characterisation $\Theta_{k+1}$ of the data set based on the decrypted gradient and the decrypted random data according to $$\Theta_{k+1} = \Theta_k + \eta_k \frac{a g_k^1 + b g_k^2 + c g_k^3}{a + b + c},$$

where η is an appropriately chosen learning factor which may be decreased each iteration. When performing gradient descent, processor 402 iteratively updates the parameters according to the gradient. The learning factor η or "step size" is typically decreased from some initial value to zero. This has the effect of allowing large changes initially (when the parameters are far from the optimal parameters) and reducing the size of the changes as they get closer to the optimum. The initial value and decay schedule are highly dependent on the data and objective function. In one example, the initial value is '0.01' and the decay is proportional to the inverse of k squared, that is $\eta_k = 0.01 \times k^{-2}$.

As can be seen from the equation above for $\Theta_{k+1}$, dividing the decrypted sum of gradients by the sum of random numbers partially reverts the alteration of the gradient based on the random data, that is, the multiplication of the partial gradients by the random numbers. This reversion is only partial and not perfect because in general terms $$\frac{ax + by}{a + b} \neq x + y.$$

However, me reversion is sufficient to allow the update of the model parameters. In particular, if the random numbers a, b and c are uniformly distributed, their influence should even out and the direction of correction of the model parameters remains close to the non-randomised result. It is noted that in some examples, the performance may be sufficient without this normalisation by the sum of random numbers.

The process described above, that is, performing method 500 on the three smartphones 602, 604 and 606 and performing method 700 on the server is repeated and in each iteration the model parameters are updated. This repetition can be stopped after a stopping criterion has been attained such as a predetermined number of iterations, such as 1000, or a sufficiently small update value, such as 10E-6.

As mentioned above, the characterisation may comprise one or more coefficients of a model, such as a linear regression model or principle components or other basis vectors for data compression.

In one example, the data set comprises data from which an anomaly or outlier is to be detected. In this example, each of the three smartphones 602, 604 and 606 determine the partial gradient of an anomaly or outlier detection system. This may not change the operation that is described above, which means that after the last iteration the final model parameters are available. Each of the three smartphones 602, 604 and 606 can then determine how far the samples of the data subsets 610, 612 and 614, respectively, are away from the regression model and can discard those samples if the distance to the regression model is above a predetermined threshold. This way, anomalies and outliers are detected and can be excluded from further consideration.

The privacy preserving gradient descent procedure can be applied to a large class of optimisation problems. The objective function is differentiable or sub-differentiable and takes the form of a sum of data provider dependent portions plus an additional parameter dependent term. The objective function does not necessarily have to be the same function for each iteration.

The procedure itself can also embody many variations. Some of these are listed below:

The number of data providers may change over time.

The data set held by each data provider may change over time.

Each data provider may provide data relating to multiple entities or individuals—for instance, each data provider may be involved in a particular industry and hold information about different sets of customers of that industry.

The learner may use a random subset of data providers during each iteration.

The number of aggregators may change over time.

The aggregation process may involve an arbitrary number of aggregators, connected in different ways, and may change over time.

The data providers may perform different random perturbations of their local gradient. They may sample multiple randomised gradient portions instead of one. They may send each portion to a different aggregator. They may omit the normalisation factors. The key property is that the expected value of the sum of the randomised gradient portions equals some multiple of the true gradient.

The data providers may take any subgradient of their local objective function when it is only subdifferentiable and not differentiable.

The procedure does not require the notion of feature vectors and labels in the objective function. These are simply to motivate the notion of privacy preservation.

The gradient descent procedure can vary. It can take account of all previous parameters, step sizes, and gradients to calculate an update.

The homomorphic cryptosystem can vary so long as it allows addition.

The procedure can perform maximisation instead of minimisation.

A more general formulation of the procedure might be as follows. Let $\Theta$ be the parameter space. Let $t \in \{1, 2, 3, \ldots\}$ be the index of the current iteration. Let $\theta_t$ be the parameters during iteration t. Let $N_t$ be the set of data providers who participate in iteration t. Let $L_{t,n}:\Theta \rightarrow \mathbb{R}$ be the local objective function for data provider $n \in N_t$ during iteration t. Let $\Omega_t: \Theta \rightarrow \mathbb{R}$ be the regulariser during iteration t.

Let $t_r(\theta) = \Sigma_{n \in N_t} L_{t,n}(\theta) + \Omega_t(\theta)$ be the global objective function during iteration t. Let $g_{t,n} \in \partial L_{t,n}(\theta_t)$ be a subgradient of $L_{t,n}$ with respect to the parameters $\theta_t$. Let $P_{t,n} = \{p_{t,n,1}, \ldots, p_{t,n,M}\}$ be a set of probability distributions for data provider n during iteration t. Let $G_{t,n} = \{g_{t,n,1}, \ldots, g_{t,n,M}\}$ be the set of gradients sampled from the distributions of $P_{t,n}$ where $g_{t,n,m}$ is distributed according to $p_{t,n,m}$.

The probability distributions may be chosen such that the expected value of the sum of the sampled gradients $E[\Sigma_{g \in G_{t,n}} g]$ is in the set $\partial L_{t,n}(\theta_t)$. The privacy preserving subgradient portions are encrypted with the learners public key and sent through an aggregation network. Each aggregator sums the encrypted vectors using homomorphic addition and forwards them on to another aggregator or the learner. The learner decrypts these and calculates the global privacy preserving gradient $g_t = \Sigma_{n \in N_t} g_{t,n} + \partial \Omega(\theta_t)$ for iteration t. At the end of the iteration the learner perform a parameter update step of the form $\theta_{t+1} = \theta_t - \alpha_t(\theta_1, \ldots, \theta_t, g_1, \ldots, g_t)$ where $\alpha_t$ calculates the update step according to the previous parameters and privacy preserving gradients.

It will be appreciated by persons skilled in the art that numerous variations and/or modifications may be made to the specific embodiments without departing from the scope as defined in the claims.

It should be understood that the techniques of the present disclosure might be implemented using a variety of technologies. For example, the methods described herein may be implemented by a series of computer executable instructions residing on a suitable computer readable medium. Suitable computer readable media may include volatile (e.g. RAM) and/or non-volatile (e.g. ROM, disk) memory, carrier waves and transmission media. Exemplary carrier waves may take the form of electrical, electromagnetic or optical signals conveying digital data steams along a local network or a publically accessible network such as the internet.

It should also be understood that, unless specifically stated otherwise as apparent from the following discussion, it is appreciated that throughout the description, discussions utilizing terms such as "estimating" or "processing" or "computing" or "calculating", "optimizing" or "determining" or "displaying" or "maximising" or the like, refer to the action and processes of a computer system, or similar electronic computing device, that processes and transforms data represented as physical (electronic) quantities within the computer system's registers and memories into other data similarly represented as physical quantities within the computer system memories or registers or other such information storage, transmission or display devices.

The present embodiments are, therefore, to be considered in all respects as illustrative and not restrictive.

The invention claimed is:

1. A method for determining a gradient of an objective function in a machine learning process to iteratively characterise a data set by a data model including model parameters, the dataset is distributed as multiple data subsets over multiple computer systems, the method comprising:
    determining by a first computer system a partial gradient of the objective function over a first data subset stored on the first computer system, the objective function characterises an error between the data model and the first data subset, the partial gradient points towards a reduction in the error between the data model and the first data subset;
    determining by the first computer system random data;
    determining by the first computer system an altered gradient by modifying the partial gradient based on the random data;
    encrypting by the first computer system the altered gradient to determine a first encrypted gradient such that one or more operations on the altered gradient can be performed based on the first encrypted gradient;
    determining by the first computer system an output gradient based on the first encrypted gradient;
    sending by the first computer system the output gradient to a receiving computer system.

2. The method of claim 1, further comprising:
    receiving by the first computer system a second encrypted gradient of the objective function over a second data subset, the second data subset being stored on one or more second computer systems different to the first computer system;
wherein determining the output gradient comprises performing the one or more operations to combine the first encrypted gradient with the second encrypted gradient.

3. The method of claim 2, wherein performing the one or more operations to combine the first encrypted gradient with the second encrypted gradient comprises adding the first encrypted gradient to the second encrypted gradient.

4. The method of claim 1, wherein
    determining random data comprises determining a random number; and
    determining the altered gradient comprises multiplying the random number with the partial gradient or adding the random number to the partial gradient.

5. The method of claim 1, further comprising:
    encrypting the random data to determine first encrypted random data;
    determining output random data based on the first encrypted random data; and
    sending the output random data to the receiving computer system.

6. The method of claim 5, further comprising:
    receiving by the first computer system second encrypted random data;
wherein determining the output random data comprises performing the one or more operations to combine the first encrypted random data with the second random data.

7. The method of claim 1, wherein determining the partial gradient is based on a regression model.

8. The method of claim 1, wherein the first data subset comprises training data for training a classifier and the training data comprises one or more samples and a label for each of the one or more samples.

9. The method of claim 8, wherein the one or more samples comprise DNA related data.

10. The method of claim 1, wherein determining the partial gradient comprises determining the partial gradient to extract principle components of the data set.

11. The method of claim 10, wherein the first data subset comprises multiple images.

12. The method of claim 1, wherein the first data subset comprises training data of a recommender system and determining the partial gradient comprises determining the partial gradient of the recommender system.

13. The method of claim 1, wherein the data set comprises data from which an anomaly or outlier is to be detected and determining the partial gradient comprises determining the partial gradient of an anomaly or outlier detection system.

14. The method of claim 1, wherein the first data subset or the second data subset or both consist of a single data record.

15. The method of claim 1, wherein encrypting the altered gradient comprises using Paillier encryption.

16. A non-transitory computer readable medium comprising computer-executable instructions stored thereon, that when executed by a processor, causes the processor to perform a method of determining a gradient of an objective function in a machine learning process to iteratively characterise a data set by a data model including model parameters, the dataset is distributed as multiple data subsets over multiple computer systems, the method comprising:
    determining by a first computer system a partial gradient of the objective function over a first data subset stored on the first computer system, the objective function characterises an error between the data model and the first data subset, the partial gradient points towards a reduction in the error between the data model and the first data subset;
    determining by the first computer system random data;
    determining by the first computer system an altered gradient by modifying the partial gradient based on the random data;

encrypting by the first computer system the altered gradient to determine a first encrypted gradient such that one or more operations on the altered gradient can be performed based on the first encrypted gradient;

determining by the first computer system an output gradient based on the first encrypted gradient;

sending by the first computer system the output gradient to a receiving computer system.

17. A computer system for determining a gradient of an objective function in a machine learning process to iteratively characterise a data set by a data model including model parameters, the dataset is distributed as multiple data subsets over multiple computer systems, the computer system comprising:

a datastore to store a first data subset;

a processor to determine a partial gradient of the objective function over the first data subset, the objective function characterises an error between the data model and the first data subset, the partial gradient points towards a reduction in the error between the data model and the first data subset, determine random data, determine an altered gradient by modifying the partial gradient based on the random data, encrypt the altered gradient to determine a first encrypted gradient such that one or more operations on the altered gradient can be performed based on the first encrypted gradient, and determine an output gradient based on the first encrypted gradient; and an output port to send the output gradient to a receiving computer system.

* * * * *